(12) United States Patent
West et al.

(10) Patent No.: US 11,642,175 B2
(45) Date of Patent: May 9, 2023

(54) SYSTEMS AND METHODS FOR REGISTRATION USING AN ANATOMICAL MEASUREMENT WIRE

(71) Applicant: CENTERLINE BIOMEDICAL, INC., Cleveland, OH (US)

(72) Inventors: Karl J. West, Cleveland, OH (US); Vikash R. Goel, Cleveland, OH (US)

(73) Assignee: CENTERLINE BIOMEDICAL, INC., Cleveland, OH (US)

( * ) Notice: Subject to any disclaimer, the term of this patent is extended or adjusted under 35 U.S.C. 154(b) by 631 days.

(21) Appl. No.: 16/684,139

(22) Filed: Nov. 14, 2019

(65) Prior Publication Data

US 2020/0155239 A1 May 21, 2020

Related U.S. Application Data

(60) Provisional application No. 62/767,884, filed on Nov. 15, 2018.

(51) Int. Cl.
*A61B 34/20* (2016.01)
*A61B 34/10* (2016.01)
(Continued)

(52) U.S. Cl.
CPC ............ *A61B 34/20* (2016.02); *A61B 5/6847* (2013.01); *A61B 34/10* (2016.02); *G06F 30/20* (2020.01);
(Continued)

(58) Field of Classification Search
CPC .................................................. A61B 34/20
(Continued)

(56) References Cited

U.S. PATENT DOCUMENTS 10,575,907 B2 * 3/2020 Dekel .................... A61B 34/20
2008/0103545 A1 * 5/2008 Bolea ................... A61N 1/3606
607/42

(Continued)

FOREIGN PATENT DOCUMENTS

EP 1504713 A1 2/2005
WO 2013173234 A1 11/2013
(Continued)

OTHER PUBLICATIONS

Applicant: Centerline Biomedical, Inc.; International PCT Application No. PCT/US2019/061497, filed Nov. 14, 2019; International Search Report and Written Opinion; Authorized Officer: Inho Han; Date of Completion Mar. 10, 2020; 10 pp.

(Continued)

*Primary Examiner* — Javid A Amini
(74) *Attorney, Agent, or Firm* — Tarolli, Sundheim, Covell & Tummino LLP

(57) ABSTRACT

In an example, a system is disclosed for registering an anatomical model to an anatomical structure of a patient. The system includes an anatomical measurement wire ("AMW") configured to be navigated within the anatomical structure, the AMW comprising at least one sensor. A tracking system is configured to provide tracking data representing multiple positions of the sensor in a spatial coordinate system. A computing device is configured to generate a tracking point cloud based on the tracking data. The computing device is configured to register the predetermined anatomical model with the anatomical structure of the patient by matching the tracking point cloud with the model point cloud with respect to the predetermined anatomical model based on a quality metric.

23 Claims, 6 Drawing Sheets

(51) Int. Cl.
*A61B 5/00* (2006.01)
*G06F 30/20* (2020.01)

(52) U.S. Cl.
CPC . *A61B 2034/105* (2016.02); *A61B 2034/2046* (2016.02)

(58) Field of Classification Search
USPC .......................................................... 703/11
See application file for complete search history.

(56) References Cited

U.S. PATENT DOCUMENTS

| | | | | |
|---|---|---|---|---|
| 2008/0139915 | A1* | 6/2008 | Dolan | A61B 34/20 600/407 |
| 2010/0030063 | A1* | 2/2010 | Lee | A61B 5/06 600/424 |
| 2011/0160569 | A1* | 6/2011 | Cohen | G06T 19/00 600/424 |
| 2014/0276002 | A1* | 9/2014 | West | G06T 19/00 600/424 |
| 2016/0015469 | A1* | 1/2016 | Goshayesh | G06T 7/11 600/424 |
| 2016/0066794 | A1* | 3/2016 | Klinder | A61B 5/02028 600/424 |
| 2016/0239963 | A1* | 8/2016 | Kariv | A61B 6/481 |
| 2018/0078318 | A1* | 3/2018 | Barbagli | G06T 7/0012 |
| 2018/0368917 | A1* | 12/2018 | Dekel | A61B 1/009 |
| 2020/0155239 | A1* | 5/2020 | West | A61B 34/20 |

FOREIGN PATENT DOCUMENTS

| | | | |
|---|---|---|---|
| WO | 2017030915 A1 | 2/2017 | |
| WO | WO-2018129532 A1 * | 7/2018 | ......... A61B 1/00009 |
| WO | 2018144969 A1 | 8/2018 | |
| WO | WO-2018144969 A1 * | 8/2018 | ............. A61B 34/10 |
| WO | 2018195216 A1 | 10/2018 | |
| WO | WO-2019109013 A1 * | 6/2019 | ..... A61B 17/320016 |

OTHER PUBLICATIONS

Applicant: Centerline Biomedical, Inc.; "Systems and Methods for Registration Using an Anatomical Measurement Wire"; Japanese Patent Application No. 2021-5253307; Japanese Office Action; dated Jun. 24, 2022; 6 pgs.

Applicant: Centerline Biomedical, Inc.; "systems and Methods for Registration Using an Anatomical Measurement Wire"; European U.S. Appl. No. 19/885,296; Extended European Search Report; dated Jun. 28, 2022; 7 pgs.

* cited by examiner

SYSTEMS AND METHODS FOR REGISTRATION USING AN ANATOMICAL MEASUREMENT WIRE

CROSS-REFERENCE TO RELATED APPLICATION

This application claims the benefit of U.S. Provisional Patent Application 62/767,884 filed on 15 Nov. 2018, and entitled SYSTEMS AND METHODS FOR REGISTRATION USING AN ANATOMICAL MEASUREMENT WIRE, the entirety of which is incorporated herein by reference.

TECHNICAL FIELD

This disclosure relates generally to systems and methods for registration of patient geometry with an anatomical model using an anatomical measurement wire.

BACKGROUND

Medical imaging and other medical data associated with an anatomy are commonly used in a variety of applications such as, for example, in diagnosing medical conditions and in planning and performing medical procedures. Since the medical imaging and other data may be obtained from multiple sources, integrating the images and data is important in order to enable proper navigation and tracking in relation to the anatomy. In order to integrate the images and the data, registration must be performed, a process by which image and data points that correspond to the same anatomical points on the anatomy are mapped to one another. A registration may require ionizing radiation, such as fluoroscopic imaging, exposure to which may have undesirable side effects. Additionally, in some cases, a medical imaging modality, such as fluoroscopic imaging, may not be readily available.

SUMMARY

In an example, a system is disclosed for registering an anatomical model to an anatomical structure of a patient. The system includes an anatomical measurement wire ("AMW") configured to be navigated within the anatomical structure, the AMW comprising at least one sensor. A tracking system is configured to provide tracking data representing multiple positions of the sensor in a spatial coordinate system. A computing device is configured to generate a tracking point cloud based on the tracking data. The computing device is configured to register the predetermined anatomical model with the anatomical structure of the patient by matching the tracking point cloud with respect to the predetermined anatomical model based on a quality metric.

In another example, a method for registering an anatomical model to an anatomical structure is provided. The method includes storing tracking data representing a spatial position of sensors operatively coupled to an anatomical measurement wire at a plurality of locations within a lumen the anatomical structure. The method also includes generating a tracking point cloud based on the tracking data describing the anatomical measurement wire within the anatomical structure. The method also includes registering the anatomical model, corresponding to the anatomical structure, by matching points of the tracking point cloud with respect to the anatomical model based on a quality metric.

In yet another example, a computing device is configured to execute machine-readable instructions programmed to at least:
generate a tracking point cloud based on tracking data that is aggregated to represent geometry of an anatomical structure of a patient, the tracking data representing position of at least one sensor, operatively coupled to an anatomical measurement wire, which is navigated through the anatomical structure;
register a predetermined anatomical model, corresponding to the anatomical structure of the patient, to the anatomical structure of the patient by matching points of the tracking point cloud with respect to the predetermined anatomical model based on a quality metric.

DETAILED DESCRIPTION

This disclosure relates generally to a system and method for registering patient anatomy to an anatomical model using an anatomical measurement wire ("AMW"). The system and methods described herein can be employed prior to or during a medical procedure, such as an endovascular procedure. The AMW provides a means for collecting geometric information about an anatomical structure of a patient. In examples disclosed herein, for sake of consistency, the anatomical structure is described as an elongated tubular anatomical construct, such as a blood vessel. In other examples, the anatomical structure may be another lumen of an organ (e.g., intestine, esophagus, ureter, trachea, lymphatic ducts, bile ducts, etc.), and the approaches disclosed herein are equally applicable to such other structures. The AMW includes one or more sensors from which position and orientation may be determined in a spatial coordinate system. When the AMW is inserted inside a vessel of an anatomy, it provides geometric information about the vessel according to the location and orientation of each of the (one or more) AMW sensors. For example, a tracking system is configured to track the position and orientation of each AMW sensor as the AWM is move longitudinally through the anatomical structure. Information collected via the AMW is used to register a model, a medical image, or other data, to the vessel of the anatomy with a tracking system, such as for use in intraoperative guidance. Registration using the AMW enables registration of a tubular structure to a model of the anatomical structure to be performed without the use of ionizing radiation. For instance, registration of the tubular anatomical structure with the predetermined anatomical model may be performed in the absence of fluoroscopic imaging or another imaging modality (e.g., computed tomography).

Figure 1:
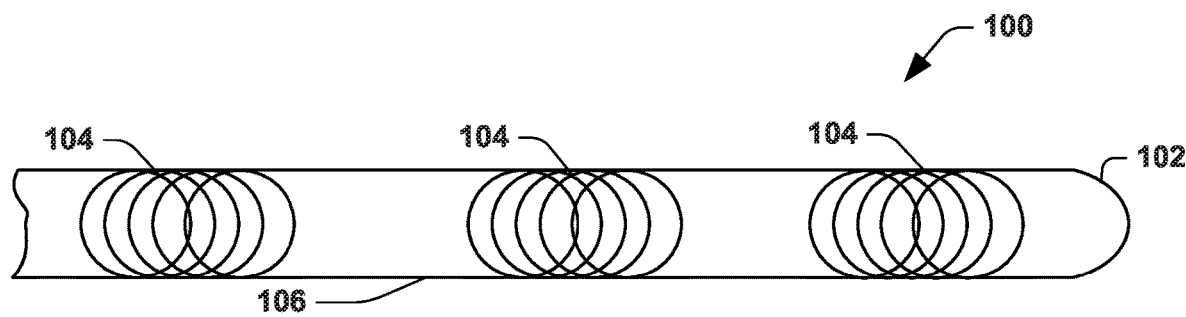
FIG. 1 illustrates an example anatomical measurement wire.

FIG. 1 illustrates an example of an elongated anatomical measurement wire ("AMW") 100. The AMW 100 can be used prior to performing a medical procedure for collecting geometric anatomical information and registering patient anatomy to a predetermined model. Once patient anatomy is registered with the model, such registration can facilitate visualizing a medical procedure in which another device (e.g., guidewire or catheter) is inserted into such patient anatomy. In one example, the medical procedure can be an endovascular procedure. Such endovascular procedures can include peripheral angioplasty, peripheral stenting or aortic aneurysm repair, among other procedures.

The AMW 100 is configured to be inserted into a patient (e.g., human or animal) and navigated through one or more anatomical structures of the patient, such as one or more vascular structures (e.g., arteries or veins) or other tubular anatomical structure. The one or more anatomical structures can comprise an elongated tubular vessel structure that includes a lumen. Alternatively, the one or more anatomical structures can include at least one blood vessel, artery, part of a gastrointestinal tract, part of a respiratory tract or part of a reproductive tract. A distal end segment 102 of the AMW 100 can be tapered to enable torquability, trackability, pushability and crossability of the AMW 100 as it is advanced longitudinally through the one or more anatomical structures. The AMW 100 can be biocompatible and be adapted to have a stiffness (e.g., measurable as a ratio of bending moment and bending) that is commensurate with an existing guidewire, such as a Glidewire® wire from Terumo Corporation® or a Lunderquirst® wire from Cook Group, Inc.

The AMW 100 includes one or more sensors 104 along a body 106 of the AMW. The one or more sensors 104 may be centrally integrated and embedded at select locations spaced apart from each other along a body 106 of the AMW 100. For example, each sensor may be mounted to an exterior wall of the AMW 100, such as fixed to a side surface or have respective coils that circumscribe around the body of the AMW. As a further example, the one or more sensors 104 can be located along an axis (e.g., a centerline) of the body 106 of the AMW 100. In an example, a plurality of sensors 104 are evenly spaced along the central longitudinal axis of the body 106 of the AMW 100, such as to provide a set of sensors at spaced apart locations starting with a distal sensor adjacent a distal end 102 of the AMW 100 and one or more additional sensors spaced longitudinally apart from the distal end along the body 106. The sensors 104 may centrally integrated within the AMW 100 or be attached to an exterior of the body 106, such as by welding, with a biocompatible adhesive, or by crimping. Additionally, or alternatively, a number of sensors 104 embedded along the axis of the body 106 of the AMW 100 can be set as a function of a length of the body 106. It should be appreciated that an increase in the number of sensors 104 strengthens the robustness of the AMW 100. Because the sensors 104 are integrated inside the body 106, the AMW 100 externally resembles an existing conventional guidewire. In another example, the sensors 104 may be attached to an exterior of the body 106, such as by welding, with a biocompatible adhesive, or by crimping.

In one example, the one or more sensors 104 can respectively spatially sense a plurality of degrees of freedom (DOF). For example, the one or more sensors 104 can be configured to sense five (5) or six (6) DOF, such as corresponding to the Aurora sensor coils available from Northern Digital Inc. In one example, the sensors 104 can be localized using an electromagnetic tracking system (see, e.g., FIG. 5), such as by each sensor generating a tracking signal based on an electromagnetic field that is generated by a field generator of the tracking system. The tracking system 502 thus enables a determination of position and orientation of each sensor 104 based on a sensor signal provided from the sensor to the tracking system in response to an electromagnetic field. Other types of tracking systems (e.g., RFID-type tracking, radiographic tracking, or fiber optic shape sensing) configured to track the position and orientation of each sensor in three-dimensional space may be used.

While inserted in vessel, the AMW 100 provides geometric information about the vessel, namely, geometric information that is based the sensor position and orientation (e.g., provided by the tracking system). For example, the position of each of the sensors 104 provides spatial information about a three-dimensional point geometrically within the vessel. In addition, the orientation of each of the sensors 104 provides an approximation of a tangent vector relative to the vessel's centerline.

The AMW 100 is further configured to be moved (e.g., pulled and/or pushed) axially through the vessel in order to obtain additional information or data points. For example, as the AMW 100 moves through vessel, the position and/or orientation of each of the sensors 104 changes and therefore new information about additional points located within the vessel is provided. The position and/or orientation of each sensor can be tracked by a tracking system at a sample rate as the AMW is moved through the vessel (or other structure). For example, the position and orientation data may be stored as 4×4 homogenous transformation matrices, as quaternions, or as pairs of position vectors and unit direction vectors. Such position and/or orientation provides geometric information that can be used, for example, to register a model of the vessel to the actual vessel (in its current position and configuration), as disclosed herein.

Figure 2A:
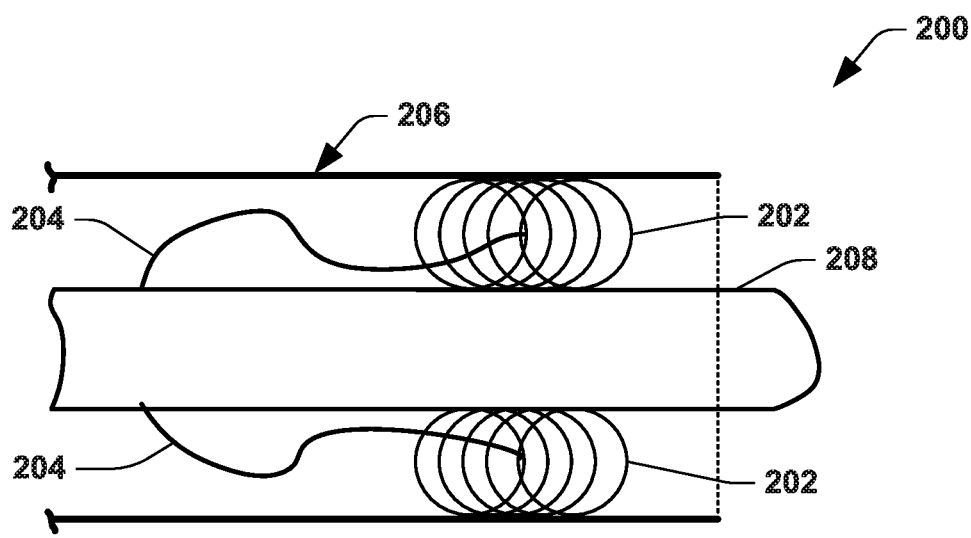
FIGS. 2A and 2B illustrate another example anatomical measurement wire.
Figure 2B:
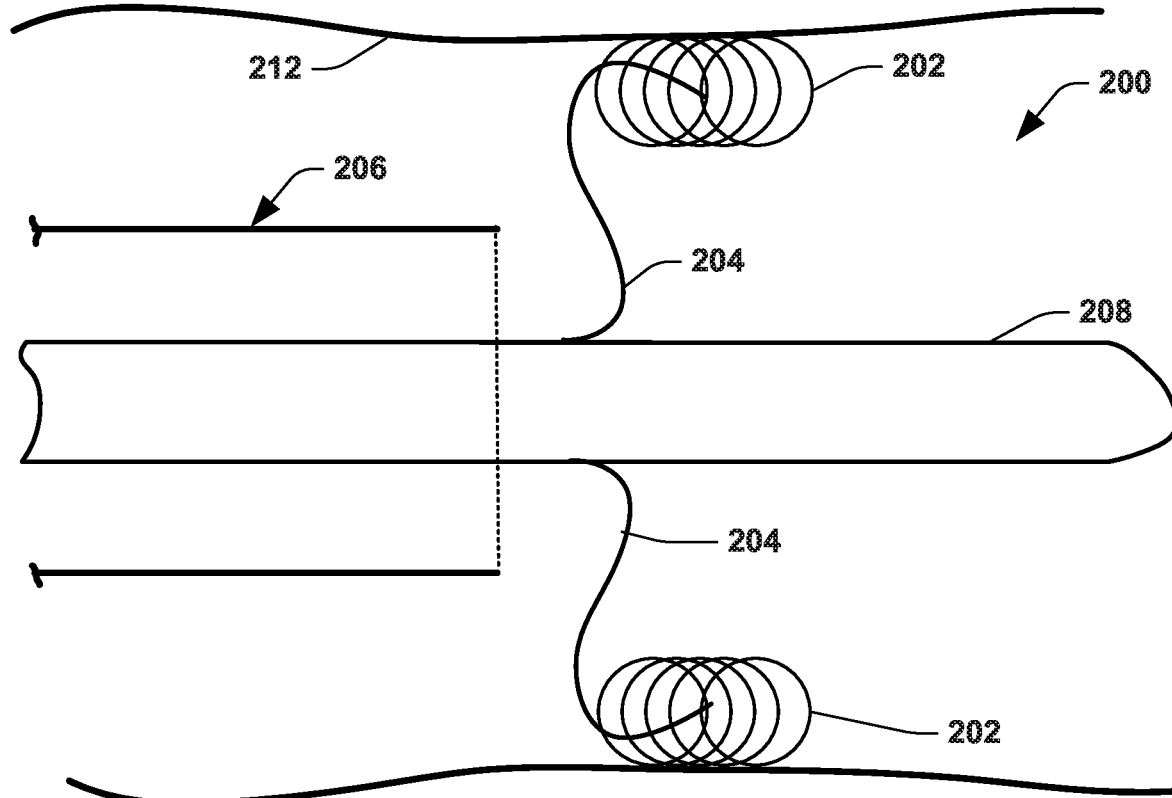

FIGS. 2A and 2B illustrate another example of an anatomical measurement wire ("AMW") 200 that includes one or more tine-mounted electromagnetic sensors 202. In the view of FIGS. 2A and 2B, two tines are shown; although different numbers of tines may be used in other examples. In this example, the sensors 202 are mounted on and/or extend from distal ends of self-expanding tines 204 that are attached to a body 208 of the AMW 200. One end of each tine is fixed to an axial location of the body 208 and the other end of the respective tine is spaced from the body by a length of the tine material. Each tine 204 is mechanically biased to urge its distal end and associated sensor 202 outwardly from the point of attachment on the body 208. Thus, in contrast to sensors 104 being fixed along the body 106 in the example of FIG. 1, the sensors in the example of FIG. 2 are moveable with respect to the body 208 of the AMW 200.

As shown in FIG. 2A, the AMW 200 can be packaged inside a catheter 206. Thus, when the catheter sidewall extends along the sensors, the sidewall constrains the tines 204 and the sensors 202 in between the catheter 206 and a body 208 of the AMW 200. The sidewall of the catheter 206 is moveable in an axial direction with respect to the AMW 200. Thus, in response to the catheter sidewall being axially relative to the AMW 200 as to not constrain the sensors (e.g., upon removal of the catheter sidewall from a radially outer extent of the respective sensors), such as shown in FIG. 2B, when placed in a tubular anatomical structure (e.g., a vessel wall) 212, the tines 204 are adapted to urge the distal end thereof and respective sensors 202 radially outwardly from the body 208. The sensors 202 thus can engage the inner sidewall of the lumen. By configuring each of the tines to apply substantially equal force between the inner wall 212 and body 208, a center of the AMW body 208 is positioned at a centroid between the distal ends of the tines, corresponding to a centerline of the anatomical tubular structure (e.g., vessel wall) 212.

As an example, each of the tines 204 is made of material having elastic properties, such as Nitinol (or other shape memory alloy), stainless steel, or another material with elastic properties. The multiple tines 204 can be spaced apart angularly around the AMW body with an evenly distributed angular spacing that depends on the number of tines located at least longitudinal location. For example, the AMW 200 may include two tines at the same longitudinal position along the length of the AMW, and spaced 180 degrees apart from each other circumferentially around the tine body. In another example, where the AMW 200 includes three tines 204, each of the tines is spaced 120 degrees apart from an adjacent tine. Where there are four tines 204, they are spaced 90 degrees apart from each other. By this even distribution of tines at one or more longitudinal location, each of the tines pushes against the interior wall 212 and bias the AMW body to align with the center of the wall structure. The tines may extend from the AMW body a length that may depend on the expected approximate size of the diameter of the vessel being measured. In small vessels for which a priori diameter information is available, the a priori diameter information may be used in lieu of measurement with the tine-mounted sensors.

For example, when the catheter 206 is retracted (e.g., while inside an anatomical structure, such as a vessel, 212), as illustrated in FIG. 2B, the tines 204 self-expand radially outwardly until they press the tines 204 in contact against inner walls of the tubular structure 212. In one example, because the sensors 202 are external to the body 208 and engaging the inner walls of the tubular structure, the AMW 200 may provide additional and improved information about the position of the sidewall 212, as compared to the AMW 100 having sensors 104 centrally integrated along the body 106, as illustrated in FIG. 1. For a multiple tine (e.g., 2 or more tines) example, the tines 204 may extend radially from the AMW body a length that is in a range from under the minimum expected diameter of the vessel to greater than the maximum expected diameter of the vessel, with an oversize intended to ensure the tines are able to reach the inner walls at the maximum and minimum vessel diameters. In this way, the material properties and configuration of the AMW 200 operate to center the body of the AMW within the tubular structure 212 when the tines are free to expand (e.g., not constrained by the catheter 206). The tines may be attached to the body of the AMW 200 such as by welding, with a biocompatible adhesive, or by crimping. The sensors may similarly be attached to the tines by any of these or similar means of attachment.

As a further example, while inserted in vessel, tracking data collected for sensors 202 of the AMW 200 provides geometric information about the vessel. In particular, the three-dimensional position of each of the sensors 202 provides spatial information about a point on the surface of the lumen of the vessel. The center of the tubular structure 212 may be readily determined (e.g., as a centroid) based on the measured spatial position (e.g., three-dimensional coordinates) of the respective sensors at a given axial position of such sensor. In an example, the geometric mean of the position measured by opposing tines at a common axial position along the body 208 (e.g., along a virtual plane extending through the respective sensors and orthogonal to the axis of the tubular structure) provides a position of a point corresponding to an estimate of the centerline of the vessel. Moreover, the mean of the orientation vectors provides a vector proximate to the tangent vector to the vessel's centerline. Thus, the AMW 200 may include one or more sets of tine-mounted sensors 202 to estimate information about the centerline. The average of the orientation vectors of the tine-mounted sensors should yield a vector that is parallel to the centerline of the vessel at the longitudinal position of the tines. Such geometric information can be used, for example, to register the vessel to an anatomical model corresponding to the vessel, as disclosed herein.

Referring again to FIGS. 2A and 2B, the tines 204 and the sensors 202 may be re-constrained to the original position as illustrated in FIG. 2B by advancing the catheter 206 over the body 208. In one example, the tines 204 are coupled to the body 208 at angles such as to permit the sensors 202 to slide along the inner walls of the vessel as the AMW 200 is retracted in the direction from which it was inserted. Depending on the material properties of the tines 204, the angles may be configured to achieve a radial force sufficient to keep the tines in contact with the walls without injuring the walls.

Figure 3A:
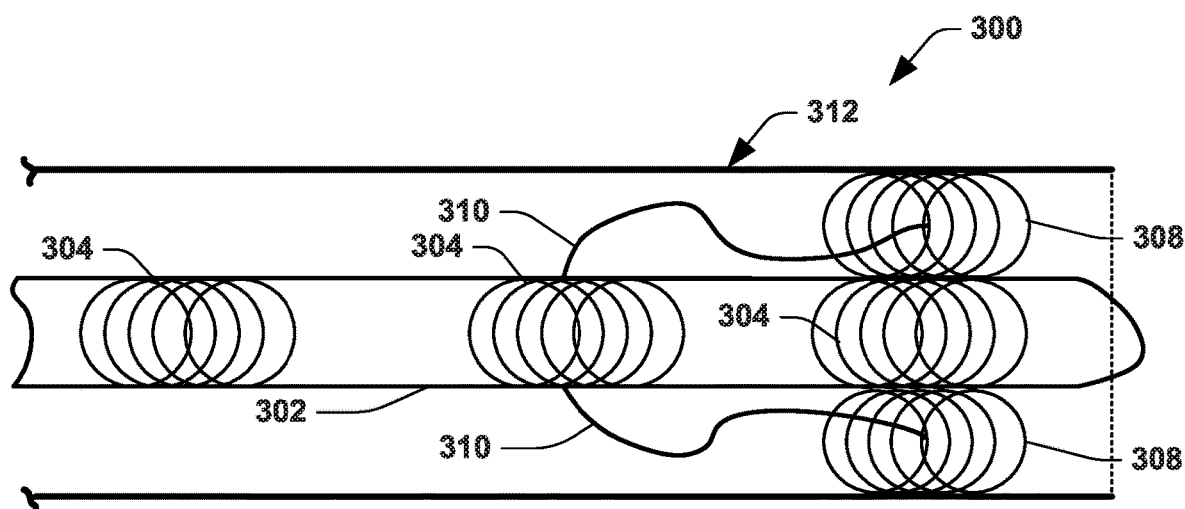
FIGS. 3A and 3B illustrate yet another example anatomical measurement wire.
Figure 3B:
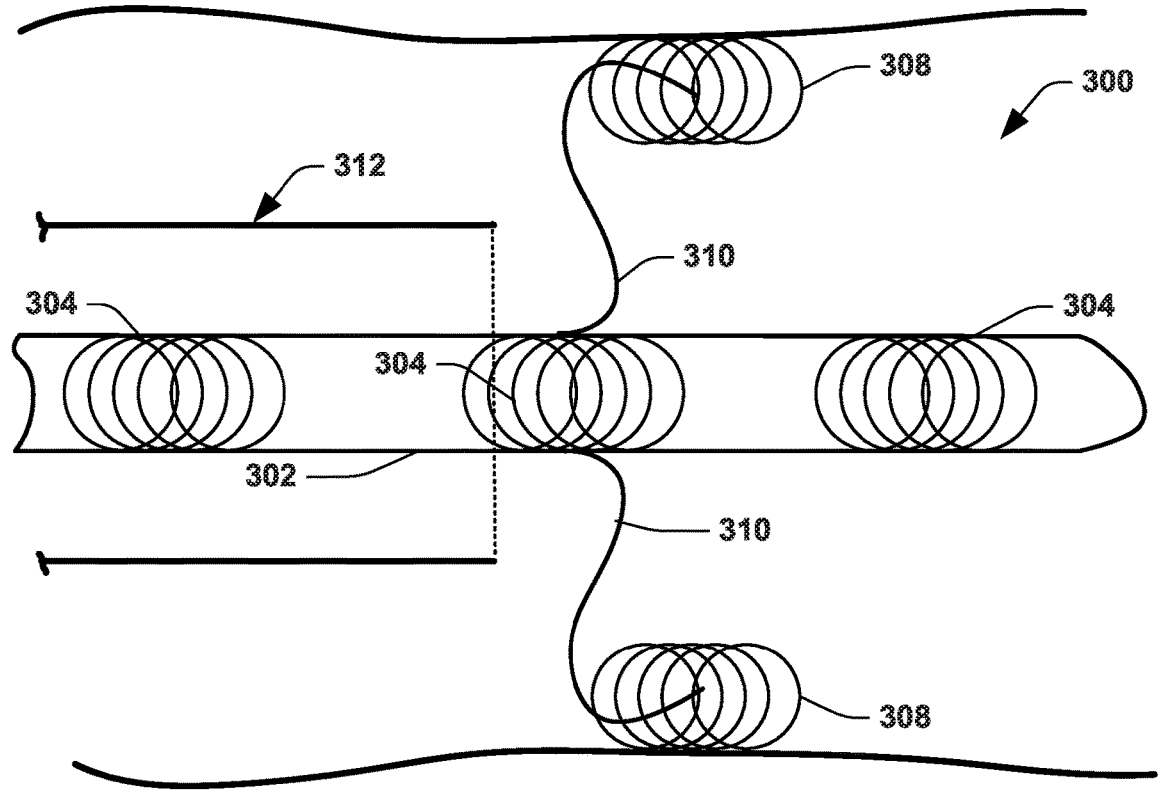

FIGS. 3A and 3B illustrate an example AMW 300 that combines the tines of the AMW 200 of FIG. 2 with the AMW 100 of FIG. 1. Thus, in this example, one or more sets of tines at axial locations along the AMW 300 help align a central body portion 302 of the AMW along the centerline of the tubular structure during use (when unconstrained—see FIG. 3B). Additionally, use of the AMW according to the method 400 enables geometry data (e.g., position and orientation information) to be collected concurrently for a set of sensors 304 on the body 302 (e.g., located proximal a centerline of the tubular structure 306) and one or more sets of sensors 308 at the end of respective tines 310 engaging the sidewall of the tubular anatomical structure 314.

In the example of FIG. 3A, the AMW 300 is in the constrained condition within a catheter 312, such that the sensors 308 are mechanically biased by respective tines 310 to engage the inner wall of the catheter 312. Thus, the catheter 312 and AMW 300 may be moved collectively as a unit (e.g., within a tubular anatomical structure 314, such as a vessel wall). Once a distal end portion of the unit is at a desired position, the catheter 312 may be pulled axially relative to the AMW 300, either by advancing the body 302 of the AMW beyond the end of the catheter or holding the AMW stationary while the catheter is retracted. Once the sensors 308 are no longer constrained, the tines 310 mechanically bias the sensors 308 radially outwardly from the body 302 and into engagement with the inner wall of tubular anatomical structure 314, such as shown in FIG. 3B. In this position, the sensors 308 are operative to provide position and orientation information along the wall of the structure 314 and the set of sensors 304 on the body 302 of the AMW 300 provide position and orientation information along a centerline within the lumen of the tubular anatomical structure 314. While the examples of FIGS. 2 and 3 show one set of moveable sensors, in other examples, more than one set of two or more moveable sensors each may be implemented on the AMW 300.

Figure 4:
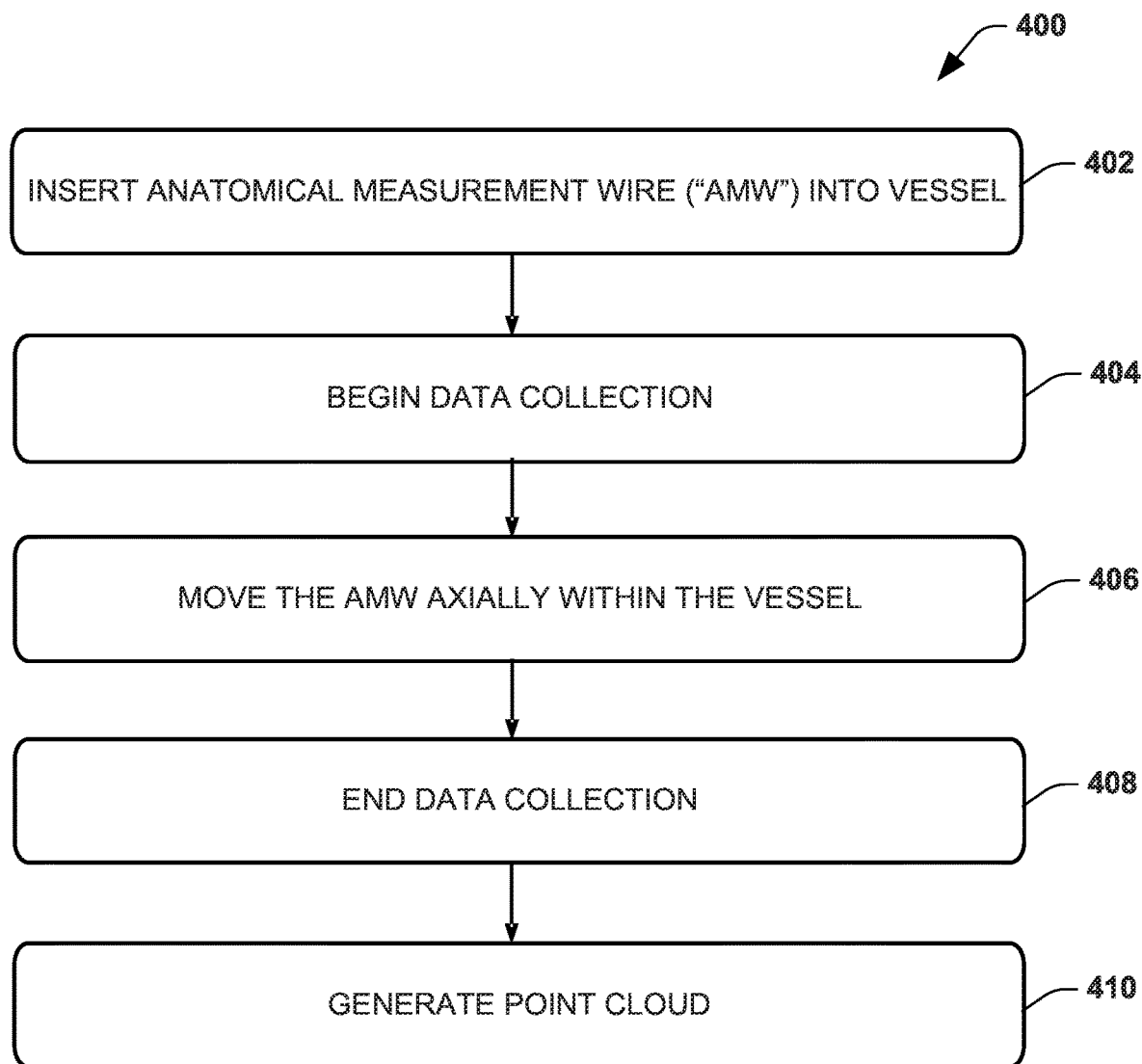
FIG. 4 illustrates an example method for using an example anatomical measurement wire.

The AMW 100 of FIG. 1, the AMW 200 of FIG. 2 and the AMW 300 of FIG. 3 will be further understood and appreciated in the context of describing an example method 400 of using an AMW, as demonstrated in FIG. 4, such as to generate a cloud of data points for an anatomical structure. While, for purposes of simplicity of explanation, the method 400 is shown and described as executing serially, the method 400 is not limited by the illustrated order, as some actions could, in other examples, occur in different orders and/or concurrently with other actions. Moreover, not all illustrated features may be required to implement the method 400 and other features disclosed herein but not shown in FIG. 4 may be used.

At 402, a user inserts the AMW into an anatomical tubular structure (e.g., vessel) of a patient. In an example, the AMW (e.g., AMW 100) is inserted through a vessel, such as to a target location or a target distance through the vessel. In another example, the AMW resides within a catheter (e.g., in a constrained condition, such as shown in FIG. 2A or 3A) to form a unit that is inserted through the vessel for placement of the AMW near the target location. It should be appreciated that the further into the tubular structure (e.g., vessel) that the AMW is inserted, the more data points the AMW will enable collection of. In one example, if accessing the vessel in a retrograde fashion, the AMW is placed as far proximally as feasible. In another example, if accessing the vessel in an antegrade fashion, the AMW is placed as far distally as feasible.

At 404, a data collection process begins. For example, a computer (e.g., computing device 500 of FIG. 5) is configured to execute software or program instructions to control collection of sensor data through communication with a tracking system that receives data from sensors of the AMW and collects data points from the sensors. The sensor data may include three-dimensional position and orientation data collected from the AMW sensors. As disclosed herein, the sensor data for a given sensor (e.g., sensor 104, 202 or 304) provides for an approximate centerline point and/or an approximate surface point when a data point is sampled or collected. The collected data points are stored by the computing device in memory. The sensor data may also be stored in memory of the tracking system.

At 406, the AMW is moved within the vessel, such as may be advanced distally or retracted proximally with respect to a user. The computer executing the program instructions continues to collect data points for each of the sensors of the AMW as the AMW is moved through the vessel. For example, the data points can be acquired by a tracking system (see, e.g., FIG. 5) that is configured to track the position and/or orientation of each sensor in a three-dimensional coordinate system. The process of collecting data points along the length of the structure from the sensors while the AMW is moved through the tubular anatomical structure allows for the collection of many more data points than there are sensors.

Aggregating this collection of data points allows for a formation of a data point cloud which can be used, for example, to register a model to the vessel. As an example, for each frame, the data collected for each sensor is a geometric transformation—a matrix that is adapted to transform from the origin of the tracking system to the origin of the sensor. Different types of tracking systems may report the tracking data in a different but mathematically equivalent form.

As an example, the transformation that forms the tracking data includes a rotation (orientation) and a translation (position) component. A calculation may be performed to separate the rotation and translation components. The translation component for a given sensor within the tubular structure may be represented as spatial coordinates, such as x, y, and z values. The coordinates representing the translation component can then be treated as the coordinates of the origin (typically the center) of the sensor. Thus, each sample from each sensor gives us one three-dimensional geometric point in space. An example of how to compute the x,y,z position from a 4×4 transformation matrix is to use the matrix to transform the homogeneous vector <0,0,0,1>.

In an example, the retraction of the AMW should be performed slowly and steadily in order to improve the accuracy of the collected data points. Moreover, a slower retraction rate may correlate to an increase in number of collected data points. Thus, the retraction rate may be determined or defined by a user based on the amount of data desired to be collected. In one example, a retraction rate may also be determined or defined by a user based on a desired sampling rate. The sampling rate may correspond to a sampling rate of an associated tracking system, for example. The user continues to retract the AMW until the most proximal sensor of the AMW is no longer within the vessel. In one example, feedback via a display or user interface is provided that corresponds to the collected data points in real time as the AMW is being extracted. Thus, a user may adjust the extraction process accordingly based on feedback received via a user interface (e.g., a device or graphical user interface).

As an example, a direct form of feedback would be to plot all of the points in the point cloud in real time, updating them on a 3-D display on the screen as each new sample is added to the point cloud. Thus the user could observe the point cloud being formed. For example, the viewing angle of such 3-D display could be made to automatically change over time to assist in appreciation of the volume of the structure being mapped.

As a further example, an additional feedback mechanism could provide means (e.g., a visualization, an audible indicator or the like) to help the operator retract the device at an appropriate speed. It could take the form of a circle on the screen that is color coded to provide feedback to the user. For example, the circle on the screen may be yellow if the retraction is being done faster or slower than is desired (exceeds a threshold speed), and red if it is too fast to generate a good data (e.g., for at least one sensor in one or more frames of tracking data). Otherwise, the visualization may remain green to indicate that the current speed is within expected parameters for generating a good data. This could, for further example, be accompanied by text appearing on the screen that might state, "Slow down!" when appropriate. For example, a user may slow down or speed up the extraction of the AMW based on received feedback if too many or too few data points are being collected.

At 408, the computer stops collecting data from the sensors. In one example, data collection ends based on user instructions to terminate the method 400. For example, a user may provide input via an interface device (e.g., a mouse, keyboard, button or switch) indicative of when the computer should stop collecting data. At 410, a point cloud is generated by aggregating the collected sensor data, which may include position and orientation data sampled at a plurality of positions along the length of the vessel as the AMW is moved axially at 406. That is, the set of points acquired over time as the AMW is moved through the vessel may be aggregated together to form a cloud of points at 410. For each given sensor that engages the interior wall of the tubular structure, the points lie on the surface of the structure (e.g., vessel wall). For a given sensor that is on the body of the AMW, the points acquired lie on a centerline for the structure (e.g., vessel centerline). The point cloud may be stored in memory as a large array of triplet values, for example. For example, as will be described below, the computing device registers an anatomical model, corresponding to the vessel, with respect to the vessel based on the point cloud generated at 410.

Figure 5:
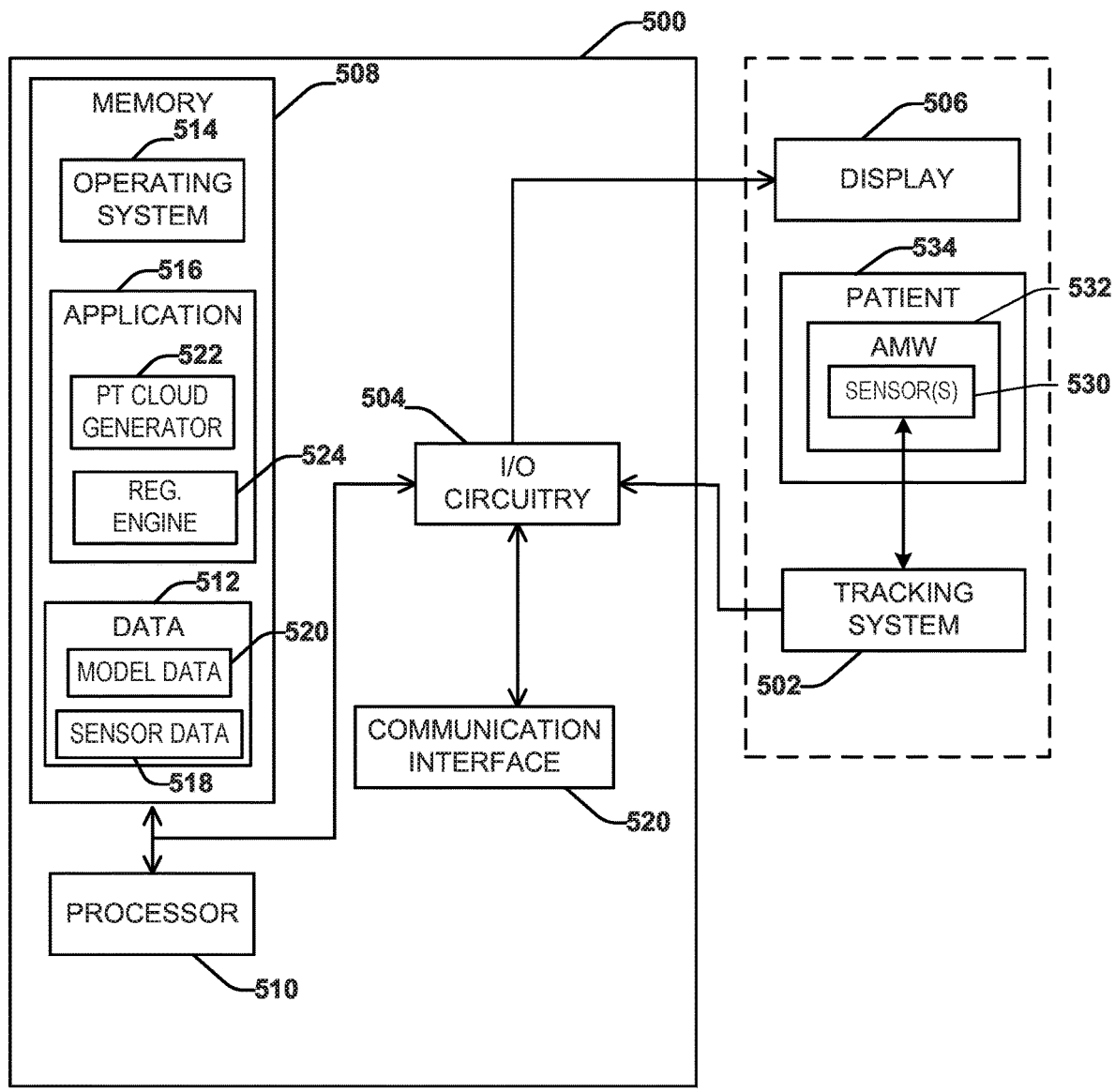
FIG. 5 illustrates an example computer for communicating with sensors of an example anatomical measurement wire.

FIG. 5 illustrates an example of a computing device 500 that can communicate a tracking system 502 via input/output (I/O) circuitry 504. The tracking system 502 is in communication with sensors 530 (e.g., sensors 104, as illustrated in FIG. 1, sensors 202, as illustrated in FIG. 2 and/or sensors 304 and 308, as illustrated in FIG. 3) of an AMW 532 (e.g. AMW 100, as illustrated in FIG. 1, and AMW 200, as illustrated in FIG. 2). The tracking system 502 and configured to provide tracking data representing position and, in some examples, orientation of the sensors 530 as they are navigated through a lumen of an anatomical structure (e.g., vessel) of the patient 534. The tracking system 502 is also configured to aggregate the tracking data to provide tracking sensor data (e.g., position and orientation data) corresponding to geometry of the anatomical structure. The tracking data may be stored in memory of the tracking system 502 and transferred to the computing device through the I/O circuitry and stored in memory 508 (e.g., as sensor data 518). As an example, the tracking system 502 is implemented as an electromagnetic tracking system, such as an electromagnetic sensing system (e.g., one of the Aurora tracking systems from Northern Digital, Inc.). Other types of tracking systems may be used in other examples in conjunction with corresponding sensors 530 for tracking 3D position as the AMW is moved transluminally within the sensing space of the respective tracking system.

For example, if the sensor data is only on the centerline (e.g., using the AMW 100), the registration is only performed using a point cloud (e.g., generated by point cloud generator from tracking data) made up of points along the centerline from the model that is being registered. If the tracking data is only on the walls of the vessels (e.g., from sensors of AMW 200), the centerline is estimated to fall along points directly between opposing tines' measurements (e.g., a mean position from the sensor position data). If the tracking data includes points along both the centerline and walls of the vessel (e.g., from sensors of AMW 300), the point cloud may be generated to include directly measured centerline data and vessel wall data. The processing and aggregation thus may be performed, as disclosed herein, such as to extract the point locations and aggregating such points to construct a large data structure of such points (a tracking point cloud). The tracking point cloud can be stored in the memory 508 as sensor data 518.

The computing device 500 can also interface with a display device 506. The display device 506 is communicatively coupled to the computing device 500 (e.g., via the I/O circuitry 504). The computing device 500 can include one or more computing apparatuses that can include a memory 508 and a processor 510. The memory 508 can be a non-transitory memory that can be configured store machine readable instructions and data 512, such as data collected from the sensors.

By way of example, the memory 508 can store a variety of machine readable instructions and the data 512, including an operating system 514, one or more application programs 516, one or more program modules 518 associated with at least one of the one or more application programs 516. The operating system 514 can be any suitable operating system or combinations of operating systems, which can depend on manufacturer and system to system corresponding to different computer manufacturers. The memory 508 can be implemented, for example as volatile memory (e.g., RAM), non-volatile memory (e.g., a hard disk, flash memory, a solid state drive or the like) or combination of both. It is to be understood that the memory 508 does not require a single fixed memory but the memory can include one or more non-transitory machine readable memory (e.g., volatile and/or non-volatile memory devices) that can store data and instructions.

The memory 508 can store data 512 and/or instructions corresponding to the operating system 514 and/or the one or more application programs 516 in a single device or distributed across multiple devices, such as in a network or a cloud computing architecture. In one example, the data 512 can include the position and/or orientation data 518 characterizing the 3-D position and/or orientation of each of the one or more EM sensors (e.g., sensors 104, 202 or 304 and 308) as collected over time, such as while the AMW is moved within the vessel.

The memory data can also include model data 520 representing a parametric model that has been generated to implicitly represent the geometry of the tubular anatomical structure (the same anatomical structure for which the sensor data 518 is acquired). For example, a parametric model (also referred to as an implicit model) represents a geometric structure by a small number of parameters. Thus, the implicit model data 520 can represent parameters that define the geometry of a physical anatomical structure of a patient, such as may be generated based on imaging data (e.g., computed tomography or magnetic resonance imaging). In the example of a tubular anatomical structure, the parametric model can include parameters that define the geometry of a centerline and surface of the tubular anatomical structure. As an example, the model data 520 can include a centerline model representing geometry of the centerline of the anatomical structure. Additionally or alternatively, the model data 520 can include a surface model describing a surface of the lumen anatomical structure. For example, the model parameters for the centerline and can be a small set of parameters, such as geometric knots along the centerline, from which control points may be calculated. Additionally, the surface model may be implemented as a lofted b-spline (basis spline) function for the elongated tubular structure.

As an example, the model data 520 may be an implicit 3-D model of the patient's anatomical structure (e.g., a vessel) generated according to the disclosure of U.S. Patent Publication No. 2011/0026793 entitled Automated Centerline Extraction Method and Generation of Corresponding Analytical Expression and Use Thereof, which is incorporated herein by reference. Another example of generating an implicit model for tubular anatomical structures is disclosed in *Analytical centerline extraction and surface fitting using CT scans for aortic aneurysm repair*, Goel, Vikash R, Master's Thesis, Cornell University (2005), which is incorporated herein by reference. Still another example of generating implicit models for a centerline and surface of tubular anatomical structures is described in the above-incorporated U.S. patent application Ser. No. 16/265,732, which is incorporated herein by reference. Other approaches for generating the implicit model data can also be utilized, such as International Publication No. WO/2014/151651. Other types of geometric representations can also be utilized to provide the implicit model data 520. For example, parameters representing lofted ellipses or triangular meshes can be generated to provide the anatomical model data 520 representing the patient's anatomical structure of interest.

The processor 510 can access the memory 508 and execute the machine readable instructions to perform respective operations (e.g., corresponding to the operating system 514 and/or the application 516). For example, the processor 510 can access the memory 508 to access the one or more application programs 516 which may include a point cloud generator 522 and a registration engine 524. The point cloud generator 522 is programmed to construct a set of data points in 3-D space based on sensor data 518 acquired by the tracking system 502 from sensors of the AMW (e.g., using the AMW 100, 200 or 300 according to the method 400). The registration engine 524 is programmed to register the anatomical model to the vessel based on the point cloud generated (e.g., by point cloud generator 522) for the sensor data 518. As disclosed herein the sensor data may include position and orientation provided by the tracking system 502.

As a further example, the registration engine (e.g., executable instructions) 524 is programmed to register the anatomical model to the vessel based on vessel geometry described by the point cloud produced by the point cloud generator 522. In an example, the registration engine 524 is programmed to match points in the data point cloud with points from either a centerline model of the vessel or a surface model of the vessel. In another example, the registration engine 524 is programmed to match points in the cloud with points from both a centerline model and a surface model of the vessel. In yet another example, the registration engine is programmed to directly match points in target point cloud (corresponding to measured anatomical geometry) to the anatomical model. For instance, where the anatomical model is implemented as a parametric model to describe the anatomical structure (e.g., centerline and/or surface models), the model is not converted to a model point cloud, and the points of the target point cloud are fit directly to the parametric model without conversion to the model point cloud. By performing such matching, according to any of these examples, the registration engine 524 is able to compute a registration transformation by identifying a translation and rotation which, when applied to the data point cloud, maximizes the proximity of the points to a mathematical model of the centerline or the surface model that has been already generated for the patient's anatomical structure.

By way of example, the anatomical model can be transformed into a point cloud using the same techniques that are used to render the model on a computer screen. The surface and/or centerline described by the model may be evaluated using suitable techniques that are appropriate for the type of model. When being rendered to display device 506, for example, the points resulting from the evaluation may be either connected by lines (e.g., if rendering in wireframe) or triangles (e.g., if rendering with polygons). In this scenario, the points alone are all that are used for rendering a graphical representation of the model on the display. An example of matching that may be utilized is described below. The resulting registration is the transformation that successfully transforms the tracking data point cloud, which is based on tracking data collected for an AMW, into a position and orientation that is closely aligned with the model point cloud.

As a further example, to perform such matching, the registration engine 524 is configured to implement the point cloud generator 522 to sample a fixed number of points from the model 520 and generates a second point cloud corresponding to the model. The model point cloud is generated in a manner that depends on the type of model to represent the anatomical structure. For example, if the model is an array of triangles, the point cloud may be constructed using all the corner vertices of the triangles. If the model is a spline-based model, the spline centerline or the spline surface may be evaluated over the range of its parameter(s) to calculate the set of points comprising the point cloud.

The registration engine 524 is further configured to evaluate the points on the second point cloud of the model according to a defined registration quality metric. For example, the registration quality metric may be the sum of the distances between each of the points in the second point cloud of the model to the nearest point in the point cloud. Other point quality metrics that may be utilized by the registration engine include the median of the distances (instead of the sum) and/or the number of points in one point cloud that are more than a threshold distance from any points in the other point cloud. The registration engine 524 may be programmed with any number of these or other matching algorithms, such as iterative closest point, robust point matching or kernel correlation or any of the 3D point registration algorithms set forth in the open source Point Cloud Library (e.g., located at pointclouds.org). The registration engine is further configured to optimize the quality of the registration by minimizing the quality metric. Multiple quality metrics can be combined, as well, by adding or multiplying, for example.

As an example, the registration engine 524 is programmed to start the transformation with a translation that is represented by a vector from a centroid of the tracking point cloud to a centroid of the second point cloud of the model. For example, the translation may be computed by calculating the centers of mass of the two point clouds (the tracking data point cloud and the model point cloud) and taking the vector from one center of mass to the other center of mass. The registration engine 524 is configured to then perform coarse and fine tuning in order to optimize the quality metric. In particular, the registration engine performs a binary search of a three-dimensional rotation space in order to optimize the quality metric. The registration engine 524 refines the translation by performing an exhaustive search of a cube-shaped neighborhood whose dimension is the maximum of a diameter of the vessel. In one example, the registration engine may repeat one or both of coarse tuning and fine tuning in order to further refine the overall transformation to optimize the quality metric.

As a further example, because the translation begins with aligning the centers of mass of the two point clouds, a next step is to ascertain the rotational alignment. The measured point cloud (e.g., from AMW sensor data) thus is pitched, yawed, and rolled in 3-D space to correctly align with the model's point cloud. These are three dimensions which must be optimized as part of the registration process. For example, a step size is selected (e.g., by default or in response to a user input), such as one degree. The search space is discretized into steps the selected size and searched in order to find the one which yields the best value of the quality metric. This may be considered a "coarse" search, as 1 degree is a relatively large step.

A fine search may follow to improve the translation positioning, using a smaller size step, e.g., half a millimeter or less. Each possible position within an appropriate range (the diameter of the vessel) is tested, and the one with the best quality metric is chosen for the translation. This could then be followed by another finer alignment of the angle, as described above, but instead of searching the entire range in steps of 1 degree it could search a smaller range in steps of, say, 0.2 degrees. The latter two processes could then be repeated back and forth to zero in on an optimal registration.

In one example, the registration engine 524 is configured to switch between coarse and fine tuning based on a defined quality metric level. For example, the registration engine 524 may be configured to perform coarse tuning until the quality metric reaches a defined level, after which the registration engine may switch to fine tuning. In another example, the registration engine is configured to switch between coarse and fine tuning based on an accuracy level or other measure specified by the associated tracking system 502.

In a further example, the registration engine 524 may be configured to take into account centerline tangents in order to further optimize the quality metric. For example, in addition to measuring distance between points in the second point cloud of the model and points in the point cloud, the registration engine may also compare angles of tangents of centerlines. For example, the angles of tangents of centerlines may be implemented by the registration engine 524 as part of the quality metric. The quality metrics described above generally just compare the positions of points in the model to positions of points as measured by the AMW. However, each sensor may also provide a measure an orientation thereof, which is parallel to the vessel within which it resides. Each point in the geometric model can also have a tangent vector associated with it, whether that is on the centerline or on the surface of the vessel. Thus, the registration engine 524 may be configured to augment the quality metric with a term that accounts for alignment of these tangent directions. For example, in addition to measuring the distance from each model point to the nearest cloud point, the registration engine 524 may also measure the angle between the model point's tangent and the cloud point's tangent.

The application programs 516 can further include an output generator (not shown) that is configured generate visualization data, which can be provided to the display 506 to render one or more graphical representations. The output generator can generate the visualization data based on the collected and processed data points. As disclosed herein, this may include the acquisition process, including feedback to the user of the AMW during acquisition. Additionally, the output generator can be configured generate a visualization of a graphical representation of the registration process.

Figure 6:
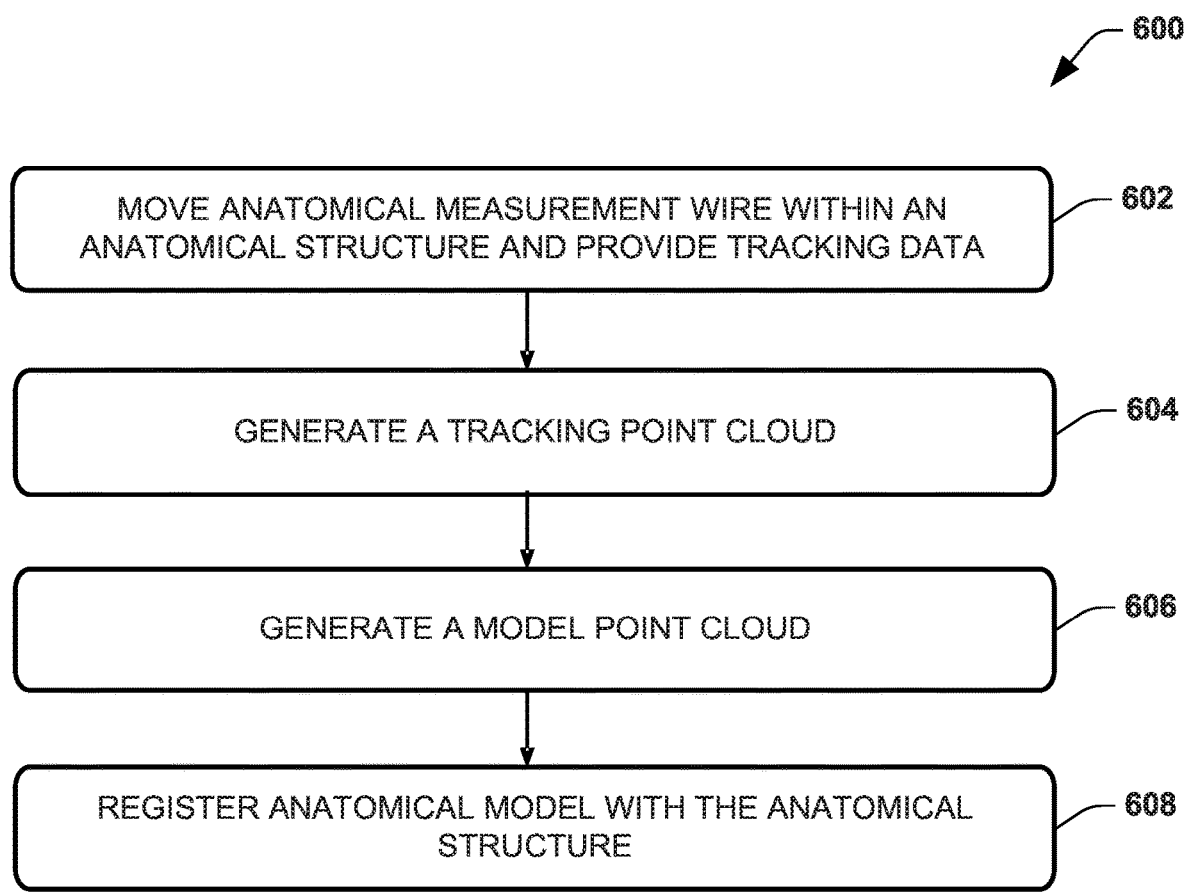
FIG. 6 illustrates an example method for registering a model to an anatomical structure based on a data point cloud obtained using an anatomical measurement wire.

In view of the foregoing structural and functional features described above, method 600 in accordance with various aspects of the present invention will be better appreciated with reference to FIG. 6. While, for purposes of simplicity of explanation, the method 600 is shown and described as executing serially, the method 600 is not limited by the illustrated order, as some actions could, in other examples, occur in different orders and/or concurrently with other actions. Moreover, not all illustrated features may be required to implement the method 600 and other features disclosed herein but not shown in FIG. 6 may be used.

FIG. 6 depicts an example method 600 for registering an anatomical model to an anatomical structure using an example anatomical measurement wire ("AMW") (e.g., AMW 100, 200 or 300). The method 600 can be implemented, for example, by a computing device (e.g., the computing device 500, as illustrated in FIG. 5). At 602, an AMW is moved within an anatomical structure. For example, the anatomical structure is a vessel or other tubular structure and the AMW is moved axially. Tracking data is generated by a tracking system to provide tracking data for the sensors (e.g., 104, 202, 304, 308) operatively coupled to a body of the AMW. In one example, the tracking data is generated via a tracking system (e.g., tracking system 502) to include 3D position and orientation in the 3D spatial coordinate system of the tracking system. In an example, the patient's body resides in the same spatial coordinate system as the tracking system, such that the tracking coordinate system is the same as the patient.

At 604, the computing device (e.g., point cloud generator 522) generates a point cloud based on tracking data (e.g., a tracking point cloud) describing the sensors of the AMW at a plurality of locations within the anatomical structure (e.g., as the AMW is moved within the structure). At 606, a second point cloud (e.g., a model point cloud) is generated (e.g., by the computing device) from a predetermined anatomical model of the anatomical structure (e.g., an analytical or parametric model). For example, the computing device samples a fixed number of points from the model, such as a set of points along the centerline and/or points along the surface of the anatomical structure. At 608, the computing device (e.g., registration engine 524) registers the anatomical model to the anatomical structure of the patient. For example, the anatomical model is registered to the patient's anatomical structure (e.g., in the spatial coordinate system of the tracking system) by matching points of the tracking point cloud with points of the model point cloud based on one or more defined quality metrics, such as described above with respect to FIG. 5. For example, the registration quality metric may be the sum of the distances between each of the points in the second point cloud to the nearest point in the point cloud. In an alternative example, the method 600 omits generating the model point cloud (at 606) and the registration process continues to 608 by registering the predetermined anatomical model directly with the target point cloud based on one or more defined quality metrics.

As a further example, the computing device is programmed to register (e.g., includes instructions to implement registration engine 524) the anatomical model based on a translation represented by a vector from a centroid of the tracking point cloud, which is derived from tracking data, to a centroid of the model point cloud. In a further example, the computing device is programmed to optimize the registration by minimizing the quality metric. In one example, the computing device optimizes the registration by performing coarse and fine tuning, such as disclosed herein. For example, the computing device performs a binary search of a two-dimensional rotation space in order to optimize the quality metric. The computing device refines the translation by performing an exhaustive search of a cube-shaped neighborhood whose dimension is the maximum of a diameter of the vessel.

A graphical representation can be generated based on the registration at 608, such as to provide a visualization on a display device. For example, the visualization includes a graphical representation of the registered model and one or more other objects that may reside within the anatomical structure of the patient (e.g., having a position specified by additional tracking data).

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system for registering an anatomical structure of a patient to a predetermined anatomical model, the system comprising:
   an anatomical measurement wire ("AMW") configured to be navigated within the anatomical structure, the AMW comprising at least one sensor;
   a tracking system configured to provide tracking data representing multiple positions of the sensor in a three-dimensional spatial coordinate system of the tracking system responsive to navigation of the AMW within the anatomical structure, the patient's body residing in the spatial coordinate system as the tracking system; and
   a computing device configured to:
      generate a tracking point cloud based on the tracking data, the tracking point cloud including a collection of points along a wall of the anatomical structure to represent a three-dimensional geometry of the anatomical structure in the spatial coordinate system of the tracking system;
      register the predetermined anatomical model with the anatomical structure of the patient by matching respective points of the tracking point cloud with the predetermined anatomical model based on a quality metric.

2. The system of claim 1, wherein the computing device is further configured to generate a model point cloud from the predetermined anatomical model, the model point cloud including a set of points corresponding to the anatomical structure of the patient, the anatomical structure of the patient being registered with the predetermined anatomical model by matching respective points of the tracking point cloud with the points of the model point cloud based on the quality metric.

3. The system of claim 1, wherein the at least one sensor of the AMW comprises a plurality of sensors at locations spaced axially apart along an elongate body of the AMW.

4. The system of claim 3, wherein the AMW further comprises a plurality of self-expanding tines extending outwardly from the body of the AMW and configured to, when located within a lumen of the anatomical structure, engage a wall of the lumen and mechanically bias the body of the AMW and the plurality of sensors along the elongate body toward alignment with a centerline of the anatomical structure.

5. The system of claim 1, further comprising a plurality of self-expanding tines extending outwardly from a body of the AMW to terminate in a distal end thereof, wherein a respective sensor is attached at the distal end of at least two of the plurality of self-expanding tines.

6. The system of claim 5, wherein the AMW resides inside a catheter and is configured to move axially with respect to the catheter, and wherein the catheter has a sidewall to constrain the plurality of tines and the plurality of sensors between an inner sidewall of the catheter and the body of the AMW.

7. The system of claim 6, wherein the anatomical structure is a tubular anatomical structure, and
   wherein the tines are mechanically biased to expand and urge respective sensors radially outwardly upon removal of the catheter sidewall from a radially outer extent of the respective sensors.

8. The system of claim 1, wherein the predetermined anatomical model comprises a parametric model including centerline model parameters to represent mathematically a centerline of the anatomical structure and surface model parameters to represent mathematically a surface of the wall of the anatomical structure.

9. The system of claim 8, wherein the computing device is further configured to:
   generate a model point cloud from the predetermined anatomical model, the model point cloud including a set of points corresponding to the anatomical structure of the patient; and
   compute a registration transformation by identifying a translation by calculating centers of mass of the tracking point cloud and the model point cloud and rotational alignment of the tracking point cloud and the model point cloud.

10. The system of claim 9, wherein the computing device is further configured to optimize the registration by minimizing the quality metric.

11. The system of claim 1, wherein the computing device is further configured to provide visual feedback based on the tracking data acquired during movement of the AMW within a lumen of the anatomical structure, the feedback being representative of whether a sufficient number of data points are collected during the movement of the AMW.

12. The system of claim 1, wherein the computing device is further configured to generate a visualization of another object relative to the predetermined anatomical model based on the registration and additional tracking data generated for the other object by the tracking system.

13. A computer-implemented method for registering an anatomical model to an anatomical structure, the method comprising:
   storing, in one or more non-transitory computer-readable media, tracking data representing a spatial position of sensors in a spatial coordinate system of a tracking system at a plurality of locations along a wall of the anatomical structure responsive to navigation of an anatomical measurement wire within the anatomical structure, the sensors being operatively coupled to the anatomical measurement wire, the patient's body residing in the spatial coordinate system of the tracking system;
   generating a tracking point cloud based on the tracking data describing the anatomical measurement wire within the anatomical structure, the tracking point cloud including a collection of points having respective coordinates in the spatial coordinate system of the tracking system and representing geometry of the wall of the anatomical structure;
   generating a model point cloud by sampling a number of points from the anatomical model, corresponding to the anatomical structure; and
   registering the anatomical model with the anatomical structure by matching respective points of the tracking point cloud with points of the model point cloud based on a quality metric.

14. The method of claim 13, wherein the anatomical model comprises a parametric model including centerline model parameters to represent mathematically a centerline of the anatomical structure and surface model parameters to represent mathematically a surface of the wall of the anatomical structure.

15. The method of claim 14, wherein the method further comprises computing a registration transformation by identifying a translation by calculating centers of mass of the tracking point cloud and the model point cloud and rotational alignment of the tracking point cloud and the model point cloud.

16. The method of claim 13, further comprising optimizing the registration by minimizing the quality metric.

17. The method of claim 13, further comprising providing visual feedback based on tracking data acquired during movement of the AMW within the lumen of the anatomical structure, the feedback being representative of whether a sufficient number of data points are collected during the movement of the AMW.

18. The method of claim 13, further comprising:
moving the anatomical measurement wire through the anatomical structure, the anatomical measurement wire including the sensors; and
generating the tracking data, via the tracking system, corresponding to position and orientation of the at least one of the plurality of sensors as the anatomical measurement wire is moved through the anatomical structure, the point cloud being derived from the tracking data.

19. The method of claim 18, wherein the anatomical measurement wire further comprises a plurality of self-expanding tines extending outwardly from a body of the anatomical measurement wire.

20. The method of claim 19, wherein the sensors are disposed on the body of the anatomical measurement wire and/or at respective distal ends of respective tines.

21. A computing device configured to execute machine-readable instructions programmed to at least:
generate a tracking point cloud based on tracking data that is aggregated to represent geometry of an anatomical structure of a patient in a spatial coordinate system of the patient, the tracking data representing position and orientation of at least one sensor, operatively coupled to an anatomical measurement wire, and collected at respective points along the anatomical structure as the anatomical measurement wire is navigated through the anatomical structure, the tracking point cloud including a collection of points along a wall of the anatomical structure to represent a three-dimensional geometry of the anatomical structure of the patient in a spatial coordinate system of the patient; and
register a predetermined anatomical model, corresponding to the anatomical structure of the patient, to the anatomical structure of the patient by matching points of the tracking point cloud with respect to the predetermined anatomical model based on a quality metric.

22. The computing device of claim 21, wherein the instructions are further programmed to
generate a model point cloud from the predetermined anatomical model, the model point cloud including a set of points corresponding to the anatomical structure of the patient, wherein the predetermined anatomical model is registered with to the anatomical structure of the patient by matching respective points of the tracking point cloud with points of the model point cloud based on the quality metric.

23. The computing device of claim 22, wherein the instructions are further programmed to compute a registration transformation by identifying a translation by calculating centers of mass of the tracking point cloud and the model point cloud and rotational alignment of the tracking point cloud and the model point cloud.

* * * * *